(12) United States Patent
Zhuang et al.

(10) Patent No.: US 11,026,691 B2
(45) Date of Patent: Jun. 8, 2021

(54) OCCULUDER

(71) Applicant: LIFETECH SCIENTIFIC (SHENZHEN) CO., LTD, Shenzhen (CN)

(72) Inventors: Shaochun Zhuang, Shenzhen (CN); Wenjun Chen, Shenzhen (CN)

(73) Assignee: LIFETECH SCIENTIFIC (SHENZHEN) CO., LTD, Shenzhen (CN)

(*) Notice: Subject to any disclaimer, the term of this patent is extended or adjusted under 35 U.S.C. 154(b) by 403 days.

(21) Appl. No.: 16/060,236

(22) PCT Filed: Jun. 15, 2016

(86) PCT No.: PCT/CN2016/085773
§ 371 (c)(1),
(2) Date: Jun. 7, 2018

(87) PCT Pub. No.: WO2017/113629
PCT Pub. Date: Jul. 6, 2017

(65) Prior Publication Data
US 2019/0000484 A1  Jan. 3, 2019

(30) Foreign Application Priority Data
Dec. 28, 2015 (CN) .......................... 201511006211.7

(51) Int. Cl.
*A61B 17/12* (2006.01)
*A61B 17/00* (2006.01)

(52) U.S. Cl.
CPC .... *A61B 17/12109* (2013.01); *A61B 17/0057* (2013.01); *A61B 17/12177* (2013.01);
(Continued)

(58) Field of Classification Search
CPC ...... A61B 17/0057; A61B 2017/00575; A61B 2017/00592; A61B 2017/00606; A61B 2017/00615
See application file for complete search history.

(56) References Cited

U.S. PATENT DOCUMENTS 6,994,717 B2   2/2006 Konya et al.
7,842,053 B2 * 11/2010 Chanduszko ...... A61B 17/0057
                                                                  606/157
(Continued)

FOREIGN PATENT DOCUMENTS

CN    101933850 A    1/2011
CN    104546054 A    4/2015
(Continued)

OTHER PUBLICATIONS

International Search Report dated Sep. 22, 2016 of corresponding International Application No. PCT/CN2016/085773; 8 pgs.
(Continued)

*Primary Examiner* — Todd J Scherbel
(74) *Attorney, Agent, or Firm* — Maier & Maier, PLLC

(57) ABSTRACT

An occluder includes a first occluder disc, a second occluder disc, a waist portion connecting the first occluder disc and the second occluder disc, and at least one soft and fibrous strand bundle structure. The strand bundle structure is disposed on at least one of a disc surface of the first occluder disc and a disc surface of the second occluder disc, the two disc surfaces faces each other, and the strand bundle structure is disposed near the waist portion. By disposing the strand bundle structure to be immediately adjacent to the waist portion, a defect opening can be occluded after implantation, thereby effectively blocking blood from flowing from one side of the defect to the other side thereof, and preventing a shunt from being formed.

17 Claims, 9 Drawing Sheets

(52) U.S. Cl.
CPC .............. *A61B 2017/00243* (2013.01); *A61B 2017/00592* (2013.01); *A61B 2017/00606* (2013.01); *A61B 2017/00623* (2013.01); *A61B 2017/00676* (2013.01); *A61B 2017/00867* (2013.01)

(56) References Cited

U.S. PATENT DOCUMENTS

| | | | | |
|---|---|---|---|---|
| 8,029,534 | B2* | 10/2011 | Hruska | .............. A61B 17/0057 606/213 |
| 8,764,772 | B2 | 7/2014 | Tekulve | |
| 2004/0143291 | A1* | 7/2004 | Corcoran | ........... A61B 17/0057 606/213 |
| 2008/0249562 | A1* | 10/2008 | Cahill | ................ A61B 17/0057 606/215 |
| 2009/0216263 | A1* | 8/2009 | Tekulve | ........... A61B 17/12177 606/200 |
| 2014/0188155 | A1 | 7/2014 | Aggerholm et al. | |

FOREIGN PATENT DOCUMENTS

| | | |
|---|---|---|
| CN | 104905828 A | 9/2015 |
| CN | 105433991 A | 3/2016 |
| DE | 233303 A1 | 2/1986 |
| EP | 2 952 157 A1 | 12/2015 |

OTHER PUBLICATIONS

Indian Office Action dated Feb. 10, 2021, in connection with corresponding in Application No. 201817023383; 6 pages.

* cited by examiner

OCCLUDER

FIELD

The present application relates to a medical device, and more particularly relates to a device for occluding a passageway or a defect or an opening in a human body, namely an occluder applicable to Patent Foramen Ovale (PFO) and also applied to occluding patent ductus arteriosus, atrial septal defect, ventricular septal defect and the like.

BACKGROUND

With continuous development of interventional devices and the interventional cardiology, a minimally invasive transcatheter occluder therapy has become an important method for treating congenital heart diseases such as atrial septal defect, ventricular septal defect, patent ductus arteriosus and patent foramen ovale. An intervention mode for endovascular occlusion is also a widely accepted treatment measure.

With reference to FIG. 1, an existing occluder 1 generally includes a first occluder disc 11, a second occluder disc 12 and a waist portion 13 connecting the first occluder disc 11 with the second occluder disc 12. After the occluder 1 is implanted into a human body, the first occluder disc 11 and the second occluder disc 12 are respectively located on two opposite sides of a passageway or a defect or an opening (which is known as the defect 2) in the human body, and cover an opening of the defect 2 to prevent blood (the flow direction of which is represented by arrow A) from flowing into the defect 2, and the waist portion 13 is located in the defect 2. If the first occluder disc 11 and/or the second occluder disc 12 are not closely fitted to a tissue wall, the blood may flow from one side of the defect 2 into the defect 2 through a gap between the occluder 1 and the tissue wall, and then flow into the other side of the defect 2. The blood flow direction is represented by arrow B in FIG. 1. This blood shunt phenomenon is called residual shunt.

The above-mentioned residual shunt phenomenon is particularly prominent in Patent Foramen Ovale (PFO) occlusion. As the PFO is a long and narrow passageway, the thickness of a septum secundum 3 is greater than that of a septum primum 4, and a tissue structure around the defect 2 has a thick upper edge and a thin lower edge. If the waist portion 13 of the occluder has a relatively large radial size or relatively low flexibility, it hardly realizes auto-deformation according to the PFO passageway, and then easily leads to the fact that the first occluder disc 11 and/or the second occluder disc 12 may not be completely fitted to the tissue wall, thereby forming a gap between the disc surface and the tissue wall, which is a passageway for residual shunt. For a relatively small residual shunt, with the gradual growth of endothelial cells, the defect 2 still may be finally occluded, but for a relatively large residual shunt, the blood would cause a change of its flow velocity when flowing through the defect 2, which may induce thrombosis, so that it needs to prolong anticoagulation therapy for a patient; and when entering blood circulation, the formed thrombi may cause severe adverse events such as embolization.

Therefore, it is desired to provide an occluder capable of obviously reducing the residual shunt.

SUMMARY

In view of the technical problems and shortcomings in the prior art, the present application provides an occluder capable of obviously reducing residual shunt.

The technical scheme for solving the technical problem is that: an occluder is provided, including a first occluder disc, a second occluder disc, and a waist portion connecting the first occluder disc with the second occluder disc. The occluder further includes at least one loosened filament bundle structure. The filament bundle structure is disposed on at least one of two opposite disc surfaces of the first occluder disc and the second occluder disc and is close to the waist portion.

According to the occluder provided by the embodiment of the present application, at least one end of the filament bundle structure is impending freely.

According to the occluder provided by the embodiment of the present application, the middle portion of the filament bundle structure is connected with the disc surface, and two ends of the filament bundle structure are impending freely.

According to the occluder provided by the embodiment of the present application, the occluder includes a plurality of lamelliform filament bundle structures distributed around the waist portion; each lamelliform filament bundle structure is wound by at least one strand of filament bundle; and the lamelliform filament bundle structures are spaced from one another or at least part of the lamelliform filament bundle structures are gathered and connected together on the disc surface.

According to the occluder provided by the embodiment of the present application, one end of at least one lamelliform filament bundle structure is connected with the disc surface, and the other end of the lamelliform filament bundle structure is impending freely; and/or the middle portion of at least one lamelliform filament bundle structure is connected with the disc surface, and two ends of the lamelliform filament bundle structure are impending freely.

According to the occluder provided by the embodiment of the present application, the occluder includes a number of woven filament bundle structures distributed around the waist portion; each woven filament bundle structure includes multiple strands of intertwined and woven filament bundles; and the woven filament bundle structures are spaced from one another or at least part of the woven filament bundle structures are gathered and connected together on the disc surface.

According to the occluder provided by the embodiment of the present application, each woven filament bundle structure axially includes a connection section and an impending section which are connected with each other; one end of the connection section is connected with the disc surface; at least one portion of the impending section is impending freely; and at least one strand of filament bundle in the impending section includes a plurality of naturally dispersed filaments.

According to the occluder provided by the embodiment of the present application, the filament bundle structures are loosely intertwined on the disc surface.

According to the occluder provided by the embodiment of the present application, the disc surface includes a filament woven structure; and the filament bundle structures are intertwined on at least one part of weaving filaments of the disc surface and/or the filament bundle structures pass through a plurality of woven grids of the disc surface in an interpenetrating manner.

According to the occluder provided by the embodiment of the present application, the filament bundle structures include a plurality of filaments which are made of a polyamide or PET (polyethylene terephthalate) material.

According to the occluder provided by the embodiment of the present application, the filament bundle structures include a plurality of filaments with a diameter of 0.01 mm to 0.2 mm.

According to the occluder provided by the embodiment of the present application, the waist portion includes at least one connection wire which connects the two opposite disc surfaces of the first occluder disc and the second occluder disc; or the waist portion includes a plurality of closed rings, and each closed ring is connected with the two opposite disc surfaces of the first occluder disc and the second occluder disc through one independent connection wire; or the waist portion is a multi-turn closed coil formed by penetrating one connection wire through the two opposite disc surfaces of the first occluder disc and the second occluder disc in a reciprocating manner.

According to the occluder provided by the embodiment of the present application, when the waist portion is maximally pulled, its long axis is in a range from 1 mm to 4 mm, and further is in a range from 1 mm to 2 mm.

According to the occluder provided by the embodiment of the present application, the filament bundle structures are at least disposed on the disc surface, which faces to the second occluder disc, of the first occluder disc; the disc surface is woven by elastic weaving filaments, and includes a central region and an edge region surrounding the central region; when the central region and the edge region are respectively compressed to the minimum in a radial direction, the maximum cross sectional area of the central region subjected to the radial compression is smaller than the minimum cross sectional area of the edge region subjected to the radial compression; and the waist portion is connected with the central region.

According to the occluder provided by the embodiment of the present application, the disc surface, which faces to the second occluder disc, of the first occluder disc includes a central hole; the first occluder disc includes a multi-order woven mesh; the central region includes a first order of woven mesh which is closest to the central hole and is woven by a number of first order weaving filaments; the edge region includes a second order of woven mesh which is jointly woven by a number of first order weaving filaments and a plurality of second order weaving filaments and is farther from the waist portion than the first order of woven mesh; and the waist portion is connected with the first order of woven mesh.

According to the occluder provided by the embodiment of the present application, the filament bundle structures are disposed on the first order of woven mesh.

According to the occluder provided by the embodiment of the present application, there are not more than 72 first order weaving filaments.

According to the occluder provided by the embodiment of the present application, the diameter of each first order weaving filament ranges from 0.08 mm to 0.15 mm.

According to the occluder provided by the embodiment of the present application, the filament bundle structures are at least disposed on the disc surface, which faces to the second occluder disc, of the first occluder disc; in a naturally unfolded state, the edge of the first occluder disc is bent towards the second occluder disc, thus forming a flange; at least one portion of the second occluder disc is sunken into a region formed by the flange in an encircling manner; or the second occluder disc is located outside the region formed by the flange in the encircling manner.

According to the occluder provided by the embodiment of the present application, the second occluder disc is a single-layer disc woven by elastic weaving filaments and includes an interlocking structure and multiple supporting rods radiating from the center; the multiple supporting rods are connected into a whole through the interlocking structure; and the whole second occluder disc is a flat structure, and all portions of the second occluder disc have uniform thickness.

According to the occluder provided by the embodiment of the present application, in a region near the center of the second occluder disc, each weaving filament of one of the multiple supporting rods is overlapped with the multiple weaving filaments of other supporting rods in sequence, thus forming the interlocking structure.

According to the occluder provided by the embodiment of the present application, the multiple supporting rods are disposed in pairs; and each pair of supporting rods is located on the same diameter of the second occluder disc.

According to the occluder provided by the embodiment of the present application, each pair of supporting rods is woven by the same group of elastic weaving filaments; the group of elastic weaving filaments of each pair of supporting rods is divided into two subgroups; and the two subgroups of elastic weaving filaments respectively bypass a central point of the interlocking structure from two sides of the central point.

According to the occluder provided by the embodiment of the present application, one section, which is close to the tail end, of each supporting rod is of a spring shape.

According to the occluder provided by the embodiment of the present application, the position, which is close to the tail end of each supporting rod, on one weaving filament of the supporting rod is of the spring shape, and the tail ends of other weaving filaments of the same supporting rod are restricted in a cavity of the spring.

According to the occluder provided by the embodiment of the present application, blunt noses are disposed at the tail ends of the supporting rods and wrap the tail ends of the weaving filaments.

According to the occluder provided by the embodiment of the present application, the second occluder disc further includes a soft membrane which covers the supporting rods and the annular interlocking structure.

According to the occluder provided by the embodiment of the present application, an included angle between two supporting rods may vary between 30 and 150 degrees.

According to the occluder provided by the present application, the filament bundle structures are closely adjacent to the waist portion and may block an opening of a defect after the occluder is implanted, thereby effectively preventing blood from flowing into the defect from one side of the defect and/or preventing the blood from passing through the defect and flowing into the other side of the defect from one side of the defect, and avoiding formation of a residual shunt. In addition, the filament bundle structures are loosened structures, so that clearance spaces in the filament bundle structures may be easily filled with influent blood to form sealed structures, and the blood contained and retained in the loosened structures may easily form thrombi which may further compact the sealed structures, thereby enhancing a blocking effect on the blood; in addition, no other extra occluding materials are needed, thereby reducing a biological risk after the implantation.

BRIEF DESCRIPTION OF THE DRAWINGS

Further descriptions are made to the present application in combination with accompanying drawings and embodiments as follows. In the drawings.

DETAILED DESCRIPTION

For the purpose of making understandings of technical features, objects and effects of the present application more clearly, detailed descriptions are made to specific implementation modes of the present application with reference to the drawings currently.

The present application provides an occluder, which includes a first occluder disc, a second occluder disc, a waist portion connecting the first occluder disc with the second occluder disc, and at least one loosened filament bundle structure. The filament bundle structure is disposed on at least one of two opposite disc surfaces of the first occluder disc and the second occluder disc and is close to the waist portion.

Each filament bundle structure is distributed close to the waist portion, and is located near an opening of a defect after the occluder is implanted, so that residual shunted blood flow may firstly flow into the filament bundle structure when entering the defect or flowing out of the defect; and in addition, clearance spaces are reserved in the loosened filament bundle structures, and may contain and retain the blood, and the contained and retained blood in these clearance spaces may easily form thrombi to form occlusion near the opening of the defect, thus preventing the blood from flowing into the defect and/or flowing out of the defect as much as possible to avoid formation of the residual shunt as much as possible. In addition, the thrombi formed by the blood flow in the filament bundle structures would lead to occlusion which may reduce the use of other sealing materials to lower the biological risk after the implantation and may further contribute to filling and repairing of the defect, thus shortening the time required for defect closure.

First Embodiment

Figure 1:
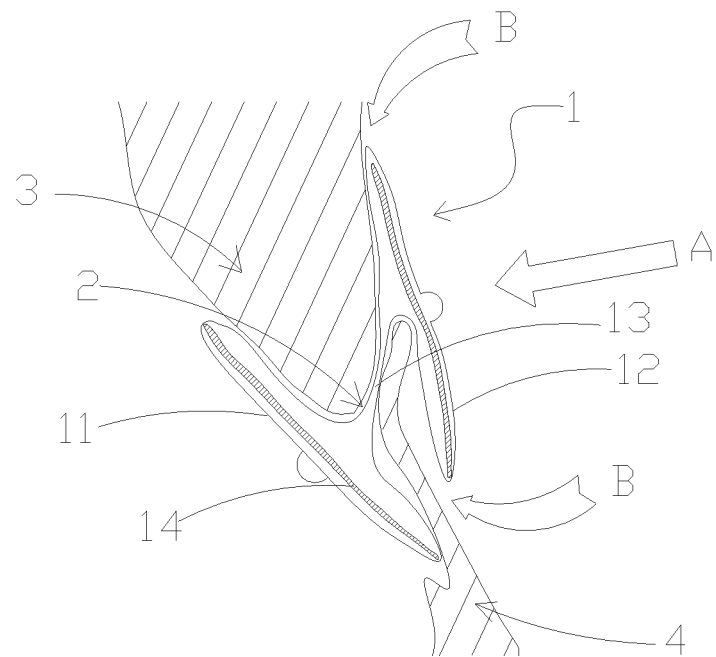
FIG. 1 is a schematic diagram of a structure of an example prior art occluder implanted into a defect.
Figure 2:
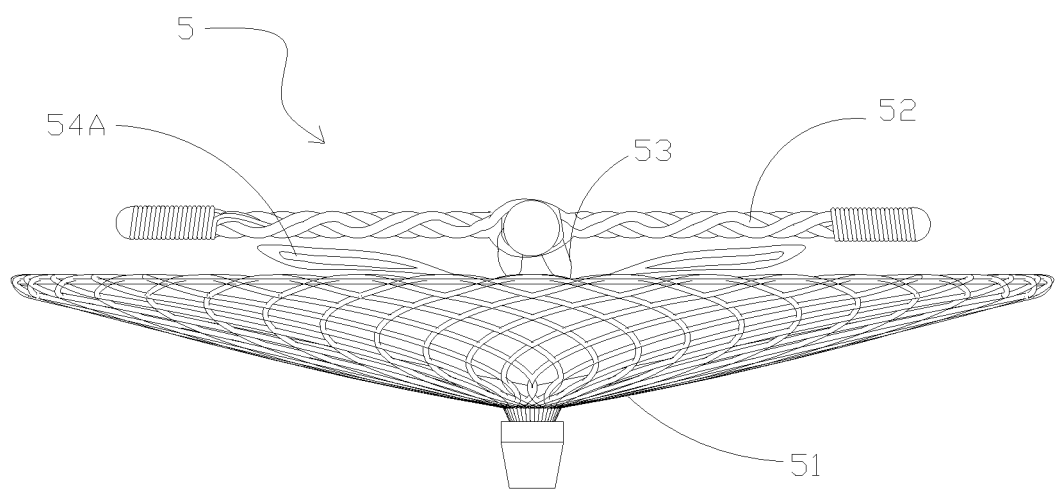
FIG. 2 is a schematic diagram of a structure of an occluder of a first embodiment of the present application.

With reference to FIG. 2, an occluder 5 according to the first embodiment of the present application includes a first occluder disc 51, a second occluder disc 52, and a waist portion 53 which is located between the first occluder disc 51 and the second occluder disc 52, and connects the first occluder disc 51 with the second occluder disc 52. The occluder 5 further includes multiple loosened lamelliform filament bundle structures 54A which are disposed on the disc surface, which is close to the waist portion 53, of the first occluder disc 51 and are close to the waist portion 53. It should be noted that in this embodiment, disposal of the filament bundle structures 54 on the first occluder disc 51 is only used as an example, but is not intended to limit the present application. For example, the filament bundle structures 54 may be also disposed on the second occluder disc 52 and are close to the waist portion 53; or the filament bundle structures 54 may be simultaneously disposed on the first occluder disc 51 and the second occluder disc 52.

Figure 3:
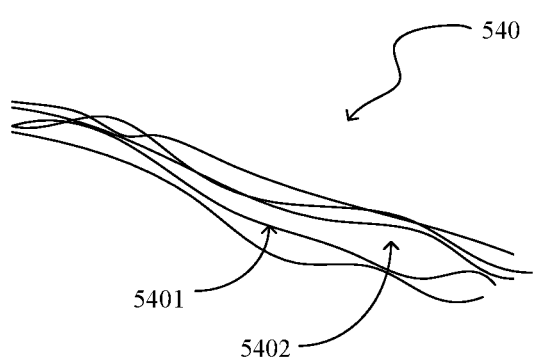
FIG. 3 is a schematic diagram of a lamelliform filament bundle structure in FIG. 2.
Figure 4:
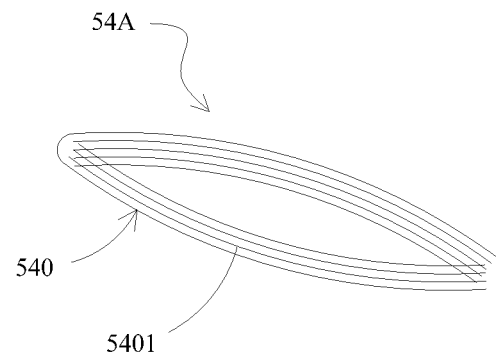
FIG. 4 is a schematic diagram of one strand of filament bundle in FIG. 3.

With reference to FIG. 3, each lamelliform filament bundle structure 54A is formed by winding at least one strand of filament bundle 540, for example, the lamelliform filament bundle structure 54A is wound into a similarly lamelliform shape. With reference to FIG. 4, the at least one strand of filament bundle 540 includes multiple loosely distributed filaments 5401, and a clearance space 5402 is formed between every two adjacent loosely distributed filaments 5401. In the one strand of filament bundle 540, the multiple filaments 5401 may be disconnected from one another, or formed by winding one continuous filament in a reciprocating manner, and there will be no clear distinguishing in the subsequent descriptions. In the one strand of filament bundle 540, there may be eight or more filaments 5401, for example ten filaments 5401; and the number of the filaments is not limited, and a person skilled in the art can select a desired or appropriate number of the filaments 5401 according to a desire to form one strand of filament bundle 540. The filaments may be made of biocompatible polyamide or a PET material. In order to form a relatively good loosened structure, a filament with a relatively small diameter is selected, for example, a filament with a diameter of 0.01 to 0.2 mm is selected. This diameter is only used as an example, and is not intended to limit the present application, and a person skilled the art can select the filaments with proper diameters according to a desire to adapt to the technology development.

Figure 5:
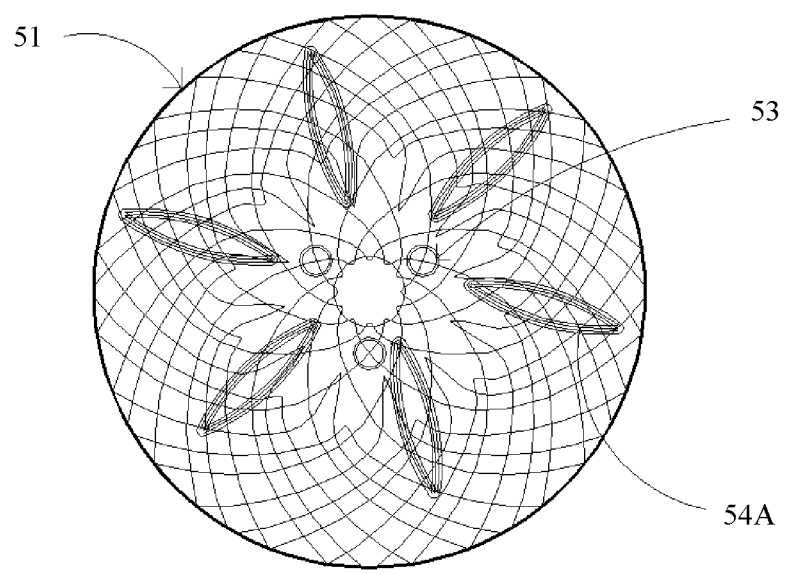
FIG. 5 is a schematic diagram of spaced distribution of the multiple lamelliform filament bundle structures in FIG. 2.

With reference to FIG. 5, in one specific implementation mode of the filament bundle structures of this embodiment, the multiple loosened lamelliform filament bundle structures 54A are spaced from one another around the waist portion (what is as shown in the figure is actually connection between the waist portion 53 and the first occluder disc 51), for example, they may be distributed in an equally spaced manner. There may be three to nine lamelliform filament bundle structures 54A, and 6 lamelliform filament bundle structures 54A are shown in the figure. The above number of the lamelliform filament bundle structures 54A is only used as example, but is not intended to limit the present application, and a person skilled in the art can set a proper number of the lamelliform filament bundle structures 54A according to an actual requirement. At least one end of each lamelliform filament bundle structure 54A is impending freely. One end of each lamelliform filament bundle structure 54A in the figure is connected with the first occluder disc 51, and the other end of the lamelliform filament bundle structure 54A is impending freely, or of course, the middle portion of each lamelliform filament bundle structure 54A is connected with the first occluder 51, and two ends of the lamelliform filament bundle structure 54A are impending freely.

Figure 6:
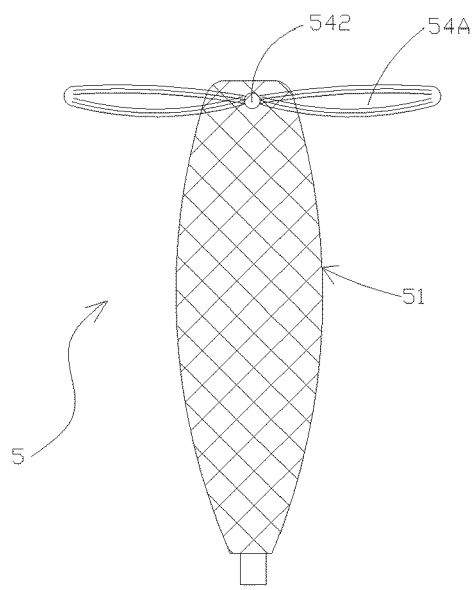
FIG. 6 is a schematic diagram of connection between the multiple gathered and connected lamelliform filament bundle structures and a first occluder disc in FIG. 2.
Figure 7:
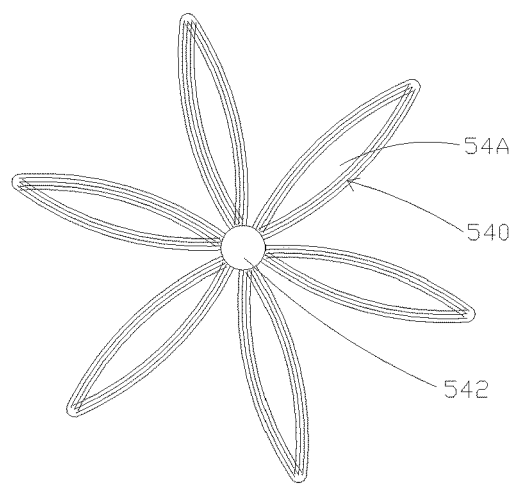
FIG. 7 is a schematic diagram of the multiple gathered and connected lamelliform filament bundle structures in FIG. 2.

FIG. 6 and FIG. 7 show another specific implantation mode of the filament bundle structures, and what is different from the above specific implementation mode is that one end of each of the multiple lamelliform filament bundle structures 54A is gathered and connected together through a central fixing member 542, and then is connected to the first occluder disc 51, and the other end of the lamelliform filament bundle structure 54A is impending freely. For example, the central fixing member 542 may be a filament which connects the lamelliform filament bundle structures 54A in series together. The central fixing member 542 is disposed on the first occluder disc 51, for example, it may be fixedly connected to the first occluder disc 51 in a filament restricting way; and the central fixing member 542 is closely adjacent to the waist portion, so that the multiple lamelliform filament bundle structures MA may be distributed in a spacing manner around the waist portion, for example, they may be distributed in an equally spaced manner. One end of each of part of the lamelliform filament bundle structures MA is gathered and connected together, and other lamelliform filament bundle structures MA are distributed at a distance from the part of the lamelliform filament bundle structures MA.

The lamelliform filament bundle structures MA have relatively large volume spaces due to their freely impending portions, which contribute to blood filling and thrombosis and the freely impending portions easily move to a defect part along with flowing of blood, and can enter a defect for filling, thereby further improving an occluding effect.

Figure 8:
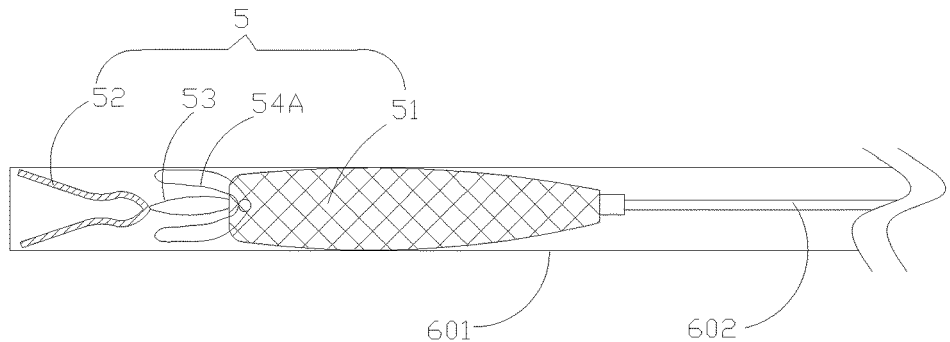
FIG. 8 is a schematic diagram of the occluder, which is compressed into a sheath, in FIG. 2.

Alternatively, FIG. 8 shows a configuration of the occluder 5 according to this embodiment, which is compressed in a radial direction and loaded into a delivery sheath 601. The first occluder disc 51 is detachably connected with a delivery steel cable 602 in the delivery sheath 601; when the delivery sheath 601 moves to a position near the defect part, the delivery steel cable 602 pushes the occluder 5 to be released from the delivery sheath 601 to occlude the defect. It can be seen from the figure that the freely impending portions of the lamelliform filament bundle structures 54A may be adaptively located in a space with a relatively small volume near the waist portion 53 in a radial compression process of the first occluder disc 51 instead of being compressed in the radial direction along with the first occluder disc 51, thereby the increase of a friction force between the first occluder disc 51 and the delivery sheath 601 may be avoided, and extra increase of the volume of the delivery sheath 601 is not needed. When the occluder 5 is released from the delivery sheath 601, even the freely impending portions of the lamelliform filament bundle structures 54A are pushed and scraped at the orifice of the delivery sheath 601 to recover their shapes and positions, the lamelliform filament bundle structures 54A are still closely adjacent to the waist portion 53 to occlude residual shunt of the defect.

Figure 9:
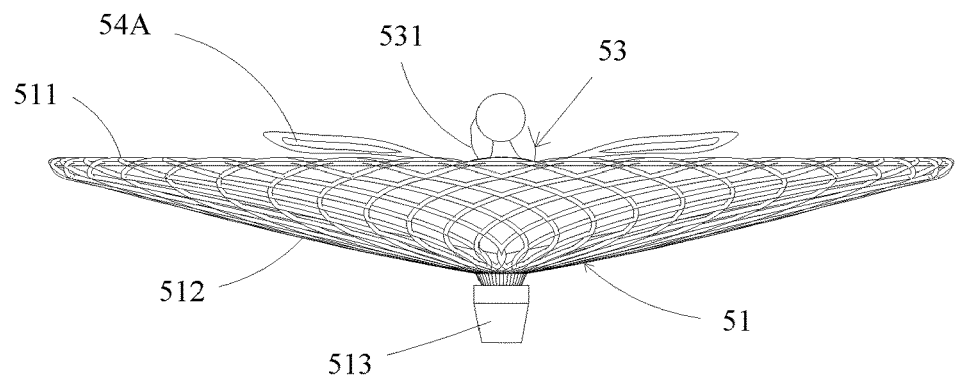
FIG. 9 is a schematic diagram of a local portion of the occluder in FIG. 2.

With reference to FIG. 9, one end of the waist portion 53 of this embodiment is movably connected with the first occluder disc 51, and the other end of the waist portion 53 is movably connected with the second occluder disc 52. The waist portion 53 may include at least one closed ring 531 formed by a connection wire with a diameter not more than 0.3 mm. The closed ring penetrates through the first occluder disc 51 and the second occluder disc 52 at the same time. By the adoption of this waist portion structure, the occluder would not occupy much space of the defect (such as a PFO "Patent Foramen Ovale" passageway) after being implanted. Further, the occluder can have a relatively high flexibility, and the waist portion 53 may adapt to the shape of the passageway to keep its flexibility.

The connection wire limits a maximum distance between the first occluder disc 51 and the second occluder disc 52. Thus, for example, when the waist portion is maximally pulled, its long axis limits the maximum distance between the first occluder disc 51 and the second occluder disc 52, for example, when the waist portion 53 is maximally pulled, its long axis may be 1 mm to 10 mm in length (which may be regarded as the length of the waist portion). In addition, the waist portion 53 may further realize angle swinging and relative position excursion between the first occluder disc 51 and the second occluder disc 52. There may be multiple closed rings 531, which are distributed in a manner of being spaced from one another. One closed ring 531 may be formed by one independent connection wire, and at this time, on the basis of maintaining a sufficient flexibility of the waist portion 53, even if a certain closed ring 531 is damaged, the connection of other independent closed rings 531 may still work. In one closed ring 531, one connection wire penetrates through the first occluder disc 51 and the second occluder disc 52 in a reciprocating manner to form a multi-turn closed coil; or one connection wire penetrates through the first occluder disc 51 and the second occluder disc 52 in a reciprocating manner to form multiple single-turn closed rings 531, so as to improve the production efficiency.

With reference to FIG. 9, the first occluder disc 51 is of a double-layer disc type structure woven by multiple elastic weaving filaments, has grids, and includes an inner side mesh 511 and an outer side mesh 512; the inner side mesh 511 is located on the side close to the waist portion 53, and it may be a planar structure; and the outer side mesh 512 is located on the side far away from the waist portion 53, and it may be a conical structure. The waist portion 53 may be connected with the inner side mesh 511, for example, the waist portion 53 may be connected with the inner side mesh 511 through woven mesh openings of the inner side mesh 511; and the lamelliform filament bundle structures 54A may be connected with the inner side mesh 511, for example, the lamelliform filament bundle structures 54A may be connected with the inner side mesh 511 through the woven mesh openings of the inner side mesh 511.

End points of all the weaving filaments forming the first occluder disc 51 are gathered at the fixed end 513 on the outer side mesh 512 of the first occluder disc 51, but no end socket for fixing all the weaving filaments to prevent all the weaving filaments from being dispersed is disposed on the inner side mesh 511 of the first occluder disc 51. Therefore, the first occluder disc 51 does not occupy the space of the waist portion 53, and the waist portion 53 may be slender, loose and flexible, which contributes to improving the adaptability of the occluder 5. The outer side mesh 512 shown in the figure is of a conical structure. It should be known that this structure is only used as an example, and is not intended to limit the present application, and a person skilled in the art can set the outer side mesh 512 as various proper structural shapes based on an instruction of the present application, for example, the outer side mesh 512 may also be of a planar structure basically parallel to the inner side mesh 511. Of course, the inner side mesh 511 of the first occluder 51 may also include the end socket for restricting and fixing all the weaving filaments.

Figure 10:
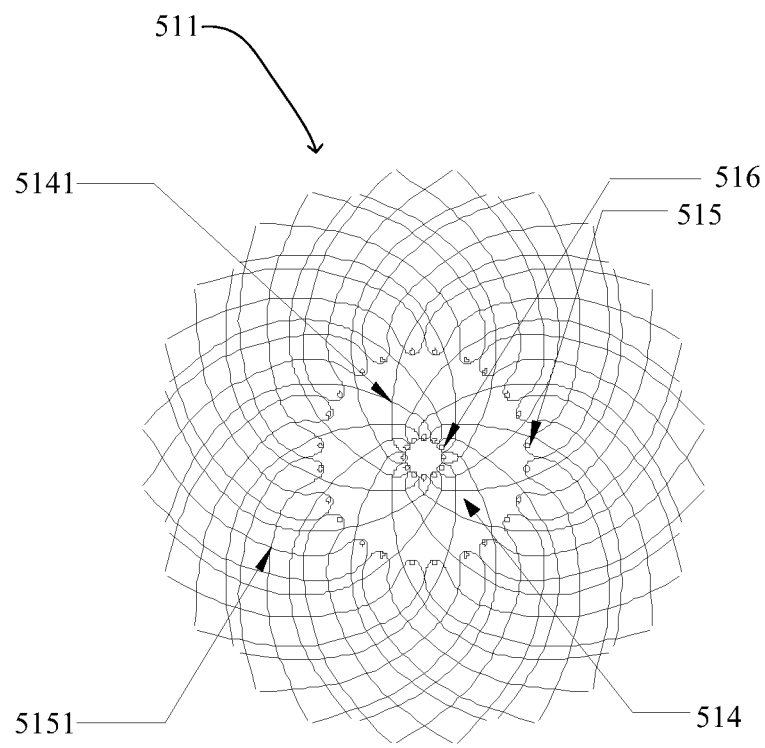
FIG. 10 is a schematic diagram of a multi-order woven structure included in the first occluder disc in FIG. 2.

With reference to FIG. 5, FIG. 9 and FIG. 10, the inner side mesh 511 of the first occluder disc 51 includes a central region 514 and an edge region 515 surrounding the central region 514, wherein the number of the weaving filaments of the central region 514 is less than that of the weaving filaments of the edge region 515.

Further, when the central region 514 and the edge region 515 are respectively compressed to the minimum in the radial direction, the maximum cross-sectional area of all the weaving filaments of the central region 514 subjected to the radial compression is smaller than the minimum cross-sectional area of all the weaving filaments of the edge region 515 subjected to the radial compression. As an example, the inner side mesh 511 does not have a structure for fixing the weaving filaments, and a central hole 516 may be further formed in a central position, which is closest to the waist portion, on the inner side mesh 511.

The structure of the first occluder disc 51 may be formed by a multi-order weaving method. The central region 514 includes a first order of woven mesh 514 woven by multiple first order weaving filaments 5141; the edge region 515 includes a second order of woven mesh 515 jointly woven by the multiple first order weaving filaments 5141 and multiple second order weaving filaments 5151; and the second order of woven mesh 515 is farther from the central hole 516 than the first order of woven mesh 514. The central hole 516 is located in the center of the first order of woven mesh 514, and is formed by the edge of the first order of woven mesh 514 in an encircling manner.

The number of the weaving filaments included in the first order of woven mesh 514 is less than that of the weaving filaments included in any other orders of woven meshes. In a naturally unfolded state, the grids of the first order of woven mesh 514 are sparser than those of any other orders of woven meshes. When each order of woven mesh is compressed to the minimum in the radial direction, the cross sectional area of the first order of woven mesh 514 subjected to the radial compression is smaller than the minimum cross sectional areas of any other orders of woven meshes subjected to the radial compression, and for example, the cross sectional area of the first order of woven mesh 514 subjected to the radial compression is smaller than the minimum cross sectional area of the second order of woven mesh subjected to the radial compression; and at this time, the maximum cross sectional area of the central region 514 is equal to the cross sectional area of the first order of woven mesh 514 subjected to the radial compression, and the minimum cross sectional area of the edge region 515 is equal to the cross sectional area of the second order of woven mesh 515.

As an example, there are not more than 72 first order weaving filaments 5141 in the first order of woven mesh 514, and the diameter of each first order weaving filament 5141 is in a range from 0.08 mm to 0.15 mm. It should be understood that in other implementation modes of the present application, multiple third order weaving filaments and even more order weaving filaments are jointly woven with the multiple first order weaving filaments 5141 and the multiple second order weaving filaments 5151 to form a first occluder disc 51 having three orders of woven mesh and even more orders of woven meshes. The edge region 515 may be the woven mesh formed by the order of weaving filaments closest to the edge of the first occluder disc 51, and the woven mesh formed by all the other weaving filaments is the central region 514; or the woven mesh formed by the order of weaving filaments closest to the central hole may be located in the central region 514, and the woven mesh formed by all the other weaving filaments is located in the edge region 515. For example, when the central region 514 including the central hole and the first order of woven mesh and the edge region 515 including the second order of woven mesh and the third order of woven mesh are compressed to the minimum in the radial direction, the maximum cross sectional area of the central region 514 is the cross sectional area of the first order of woven mesh subjected to the radial compression, and the minimum cross sectional area of the edge region 515 is the cross sectional area of the second order of woven mesh; or if the central region 514 includes the central hole, the first order of woven mesh and the second order of woven mesh, and the edge region 515 includes the third order of woven mesh, at this time, the maximum cross sectional area of the central region 514 is the cross sectional area of the second order of woven mesh subjected to the radial compression, and the minimum cross sectional area of the edge region 515 is the cross sectional area of the third order of woven mesh.

The first occluder disc 51 may be woven by a shape memory alloy, such as a nickel-titanium alloy wire, and has super elasticity after thermal treatment. The first occluder disc 51 also may be made of a metal material, such as stainless steel, or other materials which are suitable for a human body and have relatively high elasticity. The adoption of the nickel-titanium alloy wire may ensure that the first occluder disc 51 may automatically recover to an original shape after being released from the delivery sheath with a smaller diameter than itself, thereby occluding the defect and maintaining a sufficient radial supporting force. In addition, the first order of woven mesh 514 may also be made of a bioabsorbable metal material, or further include an absorbable end socket which may gather and fix the first order of woven mesh at the distal end. For example, the first order of woven mesh 514 and the end socket may be both made of pure magnesium or a medical magnesium alloy.

If the first occluder disc 51 adopts the multi-order woven structure, the lamelliform filament bundle structures 54A may be disposed on the first order of woven mesh 514, and the waist portion may be connected with the first order of woven mesh 514 to realize connection between the waist portion and the first occluder disc 51. In addition, the lamelliform filament bundle structures 54A may be distributed around the central hole 516 of the first occluder disc 51, and the waist portion may also be connected with the first occluder disc 51 around the central hole 516.

Figure 11:
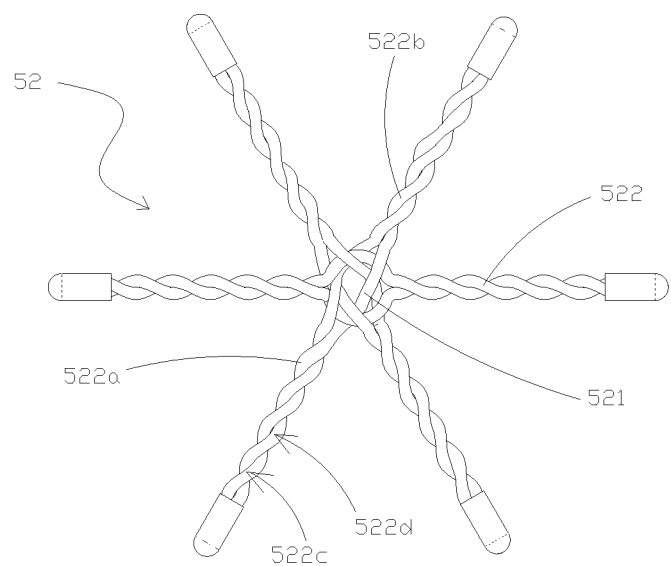
FIG. 11 is a schematic diagram of a second occluder disc in FIG. 2.

With reference to FIG. 11, the second occluder disc 52 of this embodiment is a single-layer disc woven by elastic weaving filaments and may include an interlocking structure 521 and multiple supporting rods 522 distributed in a radiating manner; the multiple supporting rods 522 are connected through the interlocking structure 521 into a whole; the whole second occluder disc 52 may be of a flat structure, and all portions of the second occluder disc 52 are uniform in thickness. In this flat structure, an included angle between two supporting rods may vary between 30 and 150 degrees.

The multiple supporting rods 522 are disposed in pairs, and each pair of supporting rods is located on the same diameter of the second occluder disc 52. To be more specific, the second occluder disc 52 includes six supporting rods 522, and two supporting rods 522 distributed on the same diameter may form one pair of supporting rods, for example, the supporting rod 522a and the supporting rod 522b form one pair of supporting rods. Each pair of supporting rods is formed by the same group of elastic weaving filaments, for example, the group of elastic weaving filaments of each pair of supporting rods is divided into two subgroups; and the two subgroups of elastic weaving filaments respectively bypass a central point of the interlocking structure from two sides of the central point. For example, one group of weaving filaments forming one pair of supporting rods, namely the supporting rod 522a and the supporting rod 522b, includes two subgroups of weaving filaments 522c and 522d.

The weaving filaments may be made of a memory alloy material having high biocompatibility, such as a nickel-titanium alloy.

It can be seen from the figure that in a region near the center of the second occluder disc 52, each weaving filament is overlapped with multiple weaving filaments of the other several groups of weaving filaments in sequence, thereby forming the interlocking structure 521 which may be an annular interlocking structure 521. The positions of the six supporting rods are relatively fixed by the interlocking structure 521, and under a condition of no extra materials for fixing, the six supporting rods form an overall flat structure. In addition, a soft membrane may be attached to the second occluder disc 52, such as a sutured polyester or PTFE (polytetrafluoroethylene) membrane, covers the supporting rods and the annular interlocking structure, and may exert an effect of quickly cutting off blood flow.

It should be known that the six supporting rods herein are only used as an example, and are not intended to limit the present application, and a person skilled in the art can select a proper number of supporting rods as desired, or make a proper deformation to supporting rod structures based on the present application to finally form the second occluder disc 52 which is overall of the flat structure and is uniform in thickness on all the portions, and the deformation and improvements based on the instruction of the present application shall fall within the scope of protection of the present application.

Second Embodiment

Figure 12:
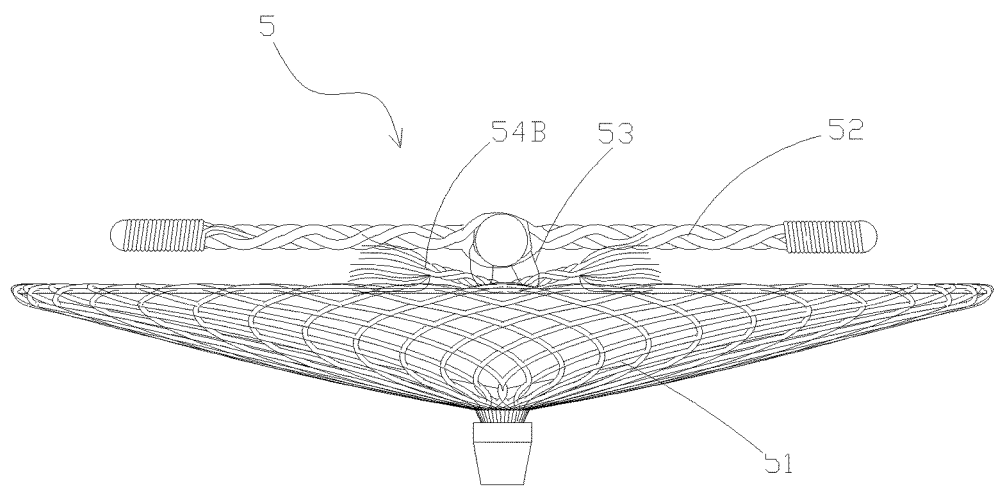
FIG. 12 is a schematic diagram of a structure of an occluder of a second embodiment of the present application.
Figure 13:
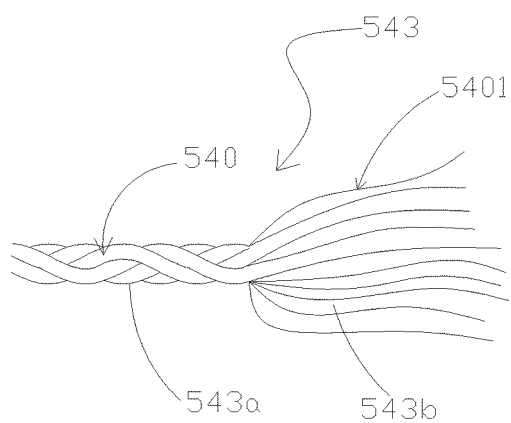
FIG. 13 is a schematic diagram of a woven filament bundle structure in FIG. 12.

FIG. 12 shows a schematic diagram of an occluder 5 according to a second embodiment of the present application, and what is different from the first embodiment is that the occluder 5 includes multiple woven filament bundle structures 54B distributed around the waist portion 53. With reference to FIG. 13, each woven filament bundle structure 54B includes multiple strands of intertwined and woven filament bundles 540; and at least one strand of filament bundle 540 includes multiple loosely distributed filaments 5401. Each woven filament bundle structure 54B axially includes a connection section 543a and an impending section 543b which are connected with each other; one end portion of the connection section 543a is connected with the first occluder disc 51 (not shown in the figure); and at least one portion of the impending section 543b is impending freely.

The multiple strands of filament bundles 540 in the connection section 543a are intertwined and woven together, for example, may be loosely intertwined and woven together. The impending section 543b includes multiple strands of filament bundles 540 which may be all from the multiple strands of filament bundles 540 of the connection section 543a, namely the connection section 543a and the impending section 543b are two portions of the same filament bundle 540; or the connection section 543a and the impending section 543b are respectively formed by mutually independent filament bundles 540. At least one strand of the filament bundle 540 in the impending section 543b includes multiple loosely distributed filaments 5401 which are naturally dispersed, instead of being intertwined and woven, and are impending freely without any restrictions. For example, the multiple strands of filament bundles 540 in the impending section 543b may all not participate in intertwining and weaving, and the filaments 5401 in all the filament bundles 540 are naturally dispersed, thereby forming a loosened structure with a larger volume than the connection section 543a on the impending section 543b.

The occluder 5 may include three to nine woven filament bundle structures 54B, and this range is only used as an example, but is not intended to limit the present application, and a person skilled in the art can select a proper number of woven filament bundle structures 54B according to an actual requirement. The multiple woven filament bundle structures 54B may be interconnected together to form a whole; or the woven filament bundle structures 54B may be distributed near the waist portion 53 in an independent spacing manner, and a person skilled in the art can set a proper distribution structure according to an implantation requirement.

Figure 14:
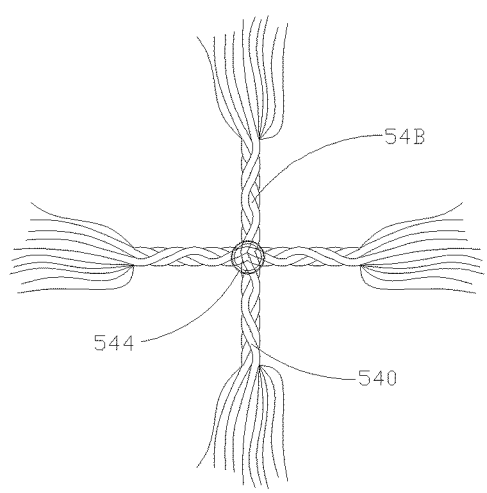
FIG. 14 is a schematic diagram of connection of the multiple woven filament bundle structures in FIG. 12 through a central fixing member.

For example, with reference to FIG. 14, the occluder 5 includes four woven filament bundle structures 54B. One end of each woven filament bundle structure 54B is connected together by a central fixing member 544, and the other end of the woven filament bundle structure 54B is impending freely. The central fixing member 544 may be a filament which connects all the woven filament bundle structures 54B in series together and is connected with the first occluder disc 51, for example, the central fixing member 544 is fixedly connected to the first occluder disc 51 in a filament restricting manner. The central fixing member 544 is closely adjacent to the waist portion 53, so that the multiple woven filament bundle structures 54B may be distributed around the waist portion 53 in a spacing manner, for example, they may be distributed in an equal spacing manner.

Figure 15:
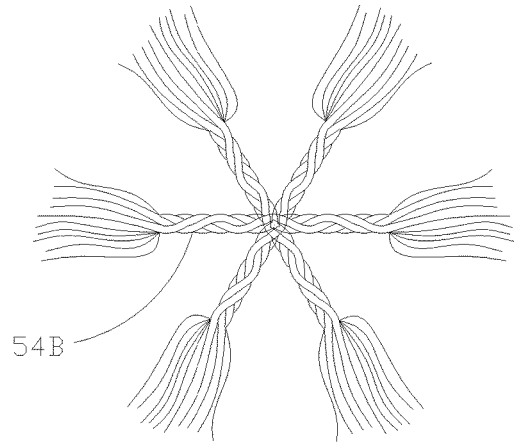
FIG. 15 is a schematic diagram of woven connection of the multiple woven filament bundle structures in FIG. 12.

For another example, with reference to FIG. 15, the occluder 5 includes six woven filament bundle structures 54B which are directly interwoven together instead of being connected together through other components (such as the above-mentioned central fixing member 544), wherein the woven interconnected region of the multiple woven filament bundle structures 54B may be located near the waist portion 53.

Third Embodiment

At least one end of each filament bundle structure in the first embodiment and the second embodiment is impending freely, and what is different is that in the third embodiment, the filament bundle structures are loosely wound on the disc surface where the filament bundle structures are disposed, such as the disc surface, which faces to the second occluder disc, of the first occluder disc.

Figure 16:
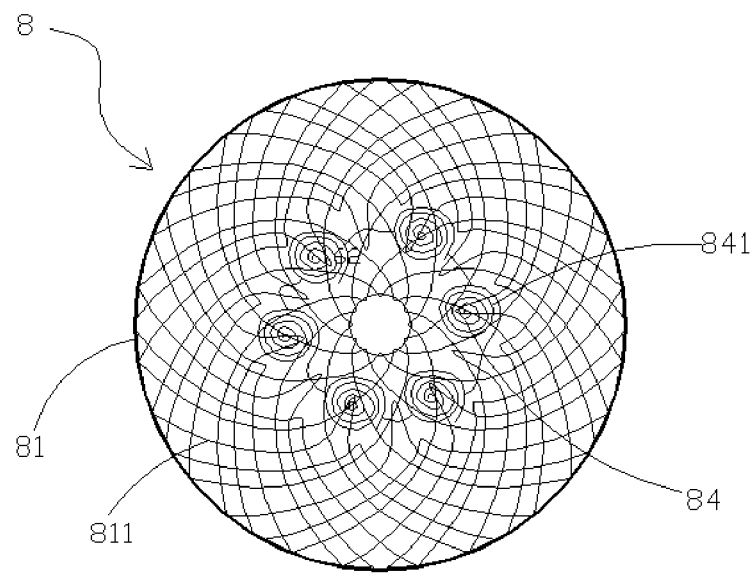
FIG. 16 is a schematic diagram of a structure of an occluder of a third embodiment of the present application.
Figure 17:
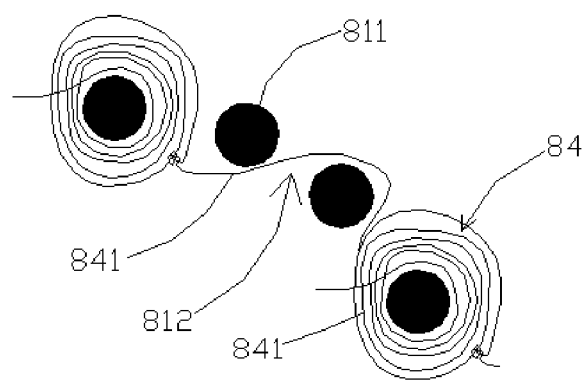
FIG. 17 is a schematic diagram of a filament bundle structure in FIG. 16.

With reference to FIG. 16 and FIG. 17, a filament bundle structure 84 of an occluder 8 includes at least one filament. The filament 841 is wound on at least part of weaving filaments 811 of a first occluder disc 81, for example, the filament may be wound on at least one weaving filament 811 in a reciprocating manner for multiple turns to form the loosened filament bundle structure. Or at least one filament 841 may pass through multiple grids 812, which is formed by the weaving filament 811, in an interpenetrating manner, for example, the filament 841 passes through the grids for many times in a reciprocating interpenetrating manner, thereby forming the loosened filament bundle structure. Or at least one filament 841 may be wound on at least one weaving filament 811, then pass through multiple grids 812, which is formed by the weaving filament 811, in an interpenetrating manner and then continuously wind another weaving filament 811, thereby finally forming the loosened filament bundle structure distributed around the waist portion (not shown in the figure).

Fourth Embodiment

Figure 18:
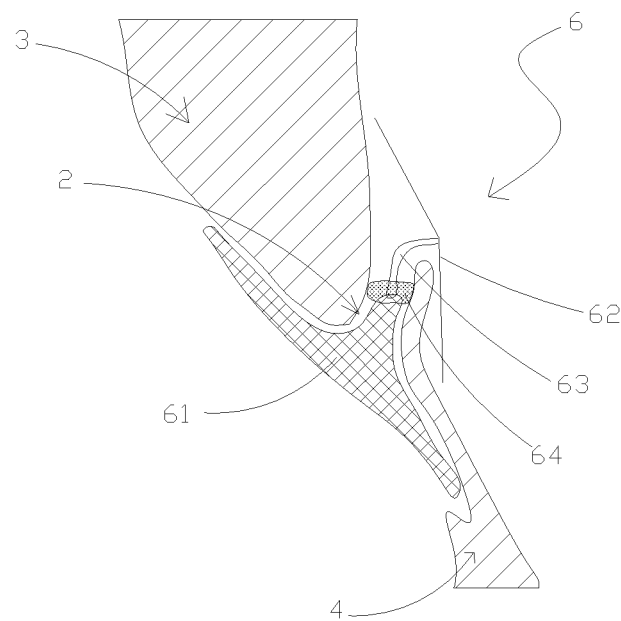
FIG. 18 is a schematic diagram of an occluder of a fourth embodiment of the present application after implantation.

With reference to FIG. 18, an occluder 6, according to the fourth embodiment, includes a first occluder disc 61, a second occluder disc 62, a waist portion 63 that is located between the first occluder disc 61 and the second occluder disc 62 and connects the first occluder disc 61 with the second occluder disc 62, and a filament bundle structure 64 which is disposed on the disc surface, which is close to the waist portion 63, of the first occluder disc 61 and is closely adjacent to the waist portion 63. On the basis of the occluder 5 or the occluder 8, it is further defined that when the waist portion 63 of the occluder 6 is maximally pulled, its long axis may be in a range from 1 mm to 5 mm in length (which may be regarded as the length of the waist portion), for example, 1 mm to 4 mm, 1 mm to 2 mm and 2 mm to 3 mm, or to be more specific, 2 mm, 3 mm, 4 mm and the like. After the occluder is implanted into a human body, the first occluder disc 61 and the second occluder disc 62 are respectively located on two opposite sides of a defect 2, and the waist portion 63 is located in the defect 2. The defect is specifically a PFO passageway. The PFO passageways of different patients are different in length due to individual differences.

When the waist portion 63 is shorter than that of the PFO passageway, one of the first occluder disc 61 and the second occluder disc 62, which easily deforms under the pulling action of the waist portion 63, is pulled by the waist portion 63 into the PFO passageway. With reference to FIG. 18, the first occluder disc 61 deforms more easily than the second occluder disc 62 under the pulling action herein, so that part of the disc surface of one side, which is connected with the waist portion 63, of the first occluder disc 61 may enter the PFO passageway 2 under the pulling action of the waist portion 63 to compensate the deficiency of the length of the waist portion 63. The compensated waist portion 63 is as long as the PFO passageway, thereby guaranteeing the stability and the occlusion performance of the occluder 6.

By the arrangement, the length applicability of the waist portion 63 of the occluder 6 may be expanded, namely the waist portion 63 with the same length may be applicable to PFO passageways 2 with different lengths. During surgery, a doctor can select the occluder 6 of a smaller specification for ordinary patients, for example, the occluder 6 with the waist portion length ranging from 1 to 2 mm may be applicable to basically all patients, and the occluder 6 with the waist portion length ranging from 1 to 4 mm may be applicable to most patients, so that the universality of the occluder 6 is improved, and such operation that the doctor had to measure the length of the PFO passageway to select the specification of the occluder is reduced or avoided as much as possible; and therefore, the surgical operation difficulty is reduced, the surgical operation time is shortened, and residual shunt caused by improper selection of the specification of the occluder 6 is further avoided, reduced, or mitigated as much as possible.

When disposed at a position, which is closely adjacent to the waist portion 63, on the first occluder disc 61, the filament bundle structure 64 would enter the PFO passageway 2 along with one portion of the first occluder disc 61. After entering the PFO passageway 2, the loosened filament bundle structure 64 may occlude a position near an opening portion of the PFO passageway 2, and blood flowing into the PFO passageway 2 may flow into the loosened filament bundle structure and form thrombi; and the thrombus-containing filament bundle structure 64 becomes a compact structure which occludes subsequent blood flow, thereby further improving the occluding effect.

If the first occluder disc 61 includes a multi-order woven structure which is the same or similar as the above-mentioned first occluder disc 51, it is more favorable for the first occluder disc 61 to enter the PFO passageway 2 to compensate the waist portion under the pulling action of the waist portion 63. That is to say, the first occluder disc 61 includes a first order of woven mesh woven by multiple first order weaving filaments and a second order of woven mesh jointly woven by the multiple first order weaving filaments and multiple second order weaving filaments; and the second order of woven mesh is farther from the waist portion 63 than the first order of woven mesh. The waist portion 63 may be connected with the first order of woven mesh to realize connection between the waist portion and the first occluder disc 61. In addition, a central hole is formed in an edge, which is closely adjacent to the waist portion 63, on the first order of woven mesh, and the waist portion 63 may be further distributed around the central hole.

After the occluder 6 is implanted, under the pulling action of the waist portion 63, the first order of woven mesh, which is relatively soft and loose, deforms more easily than other portions of the first occluder disc 61 and is easily pulled by the waist portion 63 into the PFO passageway 2, thereby avoiding the situation where the first occluder disc 61 is too hard to enter the PFO passageway and reducing wear of the weaving filaments on a tissue wall. In addition, the second order of woven mesh in the first occluder disc 61 deforms and enters the PFO passageway hardly under the pulling action of the waist portion 63 due to its greater hardness than the first order of woven mesh, which is formed by a relatively large number of weaving filaments and relatively dense woven grids, thereby preventing too many portions of the first occluder disc 61 from entering the PFO passageway, also preventing the first occluder disc 61 from entering the PFO passageway too easily, ensuring that the waist portion 63 may maintain a straining state after the implantation and avoiding the phenomenon that a connection wire of the waist portion 63 is in a loose state after the implantation; and therefore, the first occluder disc 61 and the second occluder disc 62 may both cling to the tissue wall to form effective occlusion.

Fifth Embodiment

Figure 19:
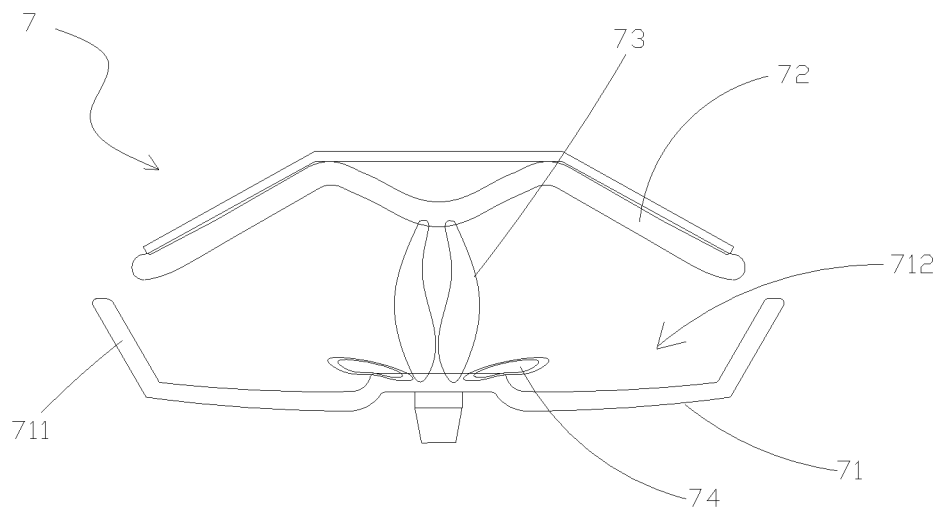
FIG. 19 is a schematic diagram of an example occluder of a fifth embodiment of the present application.
Figure 20:
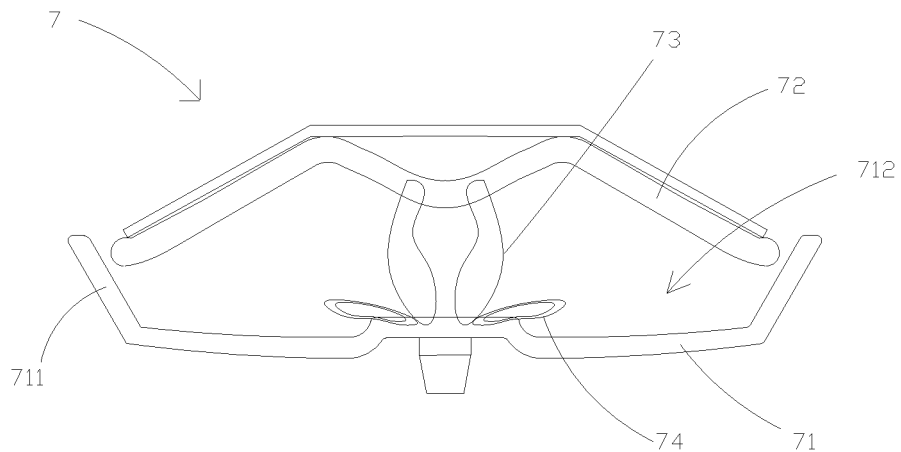
FIG. 20 is a schematic diagram of another example occluder of the fifth embodiment of the present application.

With reference to FIG. 19 and FIG. 20, an occluder 7 according to the fifth embodiment of the present application includes a first occluder disc 71, a second occluder disc 72, and a waist portion 73 which is located between the first occluder disc 71 and the second occluder disc 72 and connects the first occluder disc 71 with the second occluder disc 72. The occluder 7 further includes a filament bundle structure 74 which is disposed on the disc surface, which is close to the waist portion 73, of the first occluder disc 71 and is closely adjacent to the waist portion 73. The filament bundle structure 74 includes a loosened filament bundle structure. After the occluder is implanted into a human body, the first occluder disc 71 and the second occluder disc 72 are respectively located on two opposite sides of a defect, and the waist portion 73 is located in the defect.

On the basis of all the above-mentioned occluders (such as the occluder 5, or occluder 6, or occluder 8), in a naturally unfolded state of this occluder 7, the edge of the first occluder disc 71 is bent towards the second occluder disc 72, thus forming a flange 711. The flange 711 forms a relative region 712 in an encircling manner. The filament bundle structure 74 is located inside the region 712. The second occluder disc 72 is located outside the region 712, as shown in FIG. 19; or at least one portion of the second occluder disc 72 may be sunken into the region 712, as shown in FIG. 20.

Disposal of the flange 711 on the first occluder disc 71 may increase a clamping force between the first occluder disc 71 and the second occluder disc 72 after the occluder 7 is implanted and may also reduce the friction of the first occluder disc 71 to a contact tissue. Particularly for the occluder 7 with the relatively short waist portion 73, when one portion of the first occluder disc 71 enters the defect to compensate the length of the waist portion 73, an edge region, where the flange 711 is formed, may not deform easily, which guarantees the clamping force on the edge and not obviously enhances the friction force action of the edge region of the first occluder 71 to the contact tissue, and even provides a proper deformation allowance for the portion of the first occluder disc 71 to enter the defect, thereby ensuring that the first occluder disc 71 may compensate the waist portion and also keep an occluding shape unchanged, namely ensuring effective occlusion.

Sixth Embodiment

Figure 21:
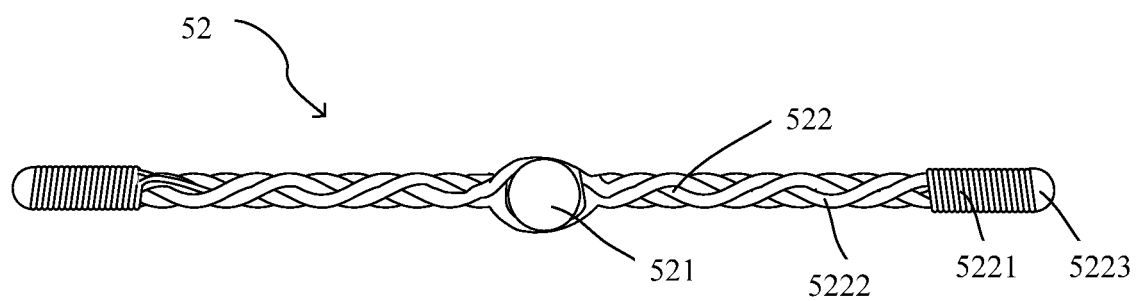
FIG. 21 is a schematic diagram of a second occluder disc of an example occluder of a sixth embodiment of the present application.
Figure 22:
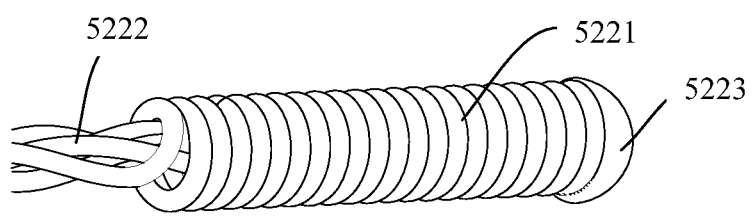
FIG. 22 is a schematic diagram of a local portion of the second occluder disc in FIG. 21.

FIG. 21 and FIG. 22 show schematic diagrams of the second occluder disc 52 according to the sixth embodiment of the present application, what is different from the second occluder disc 52 in the first embodiment is that the position, which is close to the tail end of at least one supporting rod 522, on one weaving filament of the supporting rod 522 of the second occluder disc 52 is of a spring shape, namely a tail end spring 5221 in the figure. The spring 5221 restricts the tail ends of other weaving filaments 5222 on the same supporting rod 522 in its cavity. A smooth blunt nose 5223 may be further formed at the tail end of the tail end spring 457.

In each occluder provided by the present application, the filament bundle structures are closely adjacent to the waist portion and may block the opening of the defect after the implantation, thereby effectively preventing blood from flowing into the defect from one side of the defect and/or preventing the blood from passing through the defect and flowing into the other side of the defect from one side of the defect and avoiding formation of a residual shunt. In addition, the filament bundle structures are of the loosened structures, so that clearance spaces in the filament bundle structures may be easily filled with influent blood to form sealed structures, and the blood contained and retained in the loosened structures may easily form thrombi which may further compact the sealed structures, thereby enhancing a blocking effect on the blood; and in addition, no other extra occluding materials are needed, thereby reducing a biological risk after the implantation. In addition, even if the maximum length of the waist portion of the occluder of the present application is slightly less than the length of the PFO passageway of a patient, for the purpose of adapting to a relatively long defect after the implantation, part of the disc surface of one side, which is connected with the waist portion, of the easily deforming one of the first occluder disc and the second occluder disc under the pulling action of the waist portion is pulled by the waist portion into the PFO passageway to compensate the deficiency of the length of the waist portion and improve the universality of the PFO occluder. In addition, when the loosened filament bundle structures enter the PFO passageway together with the disc surface, the residual shunt occluding performance may be further improved. In addition, formation of the bent flange at the edge of the first occluder disc may increase the clamping force between the first occluder disc and the second occluder disc after the occluder is implanted, and also may reduce the friction of the first occluder disc to the contact tissue.

Seventh Embodiment

Figure 23:
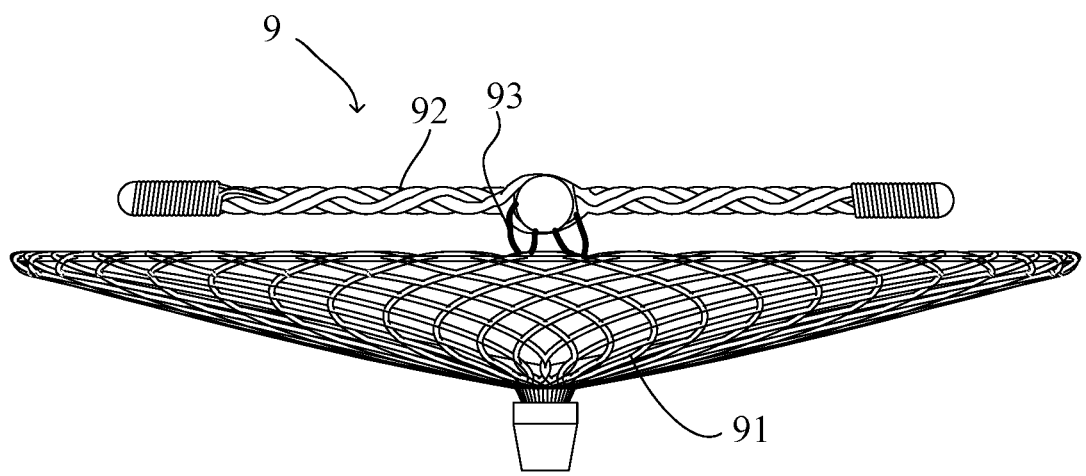
FIG. 23 is a schematic diagram of an occluder of a seventh embodiment of the present application.

With reference to FIG. 23, an occluder 9 according to the seventh embodiment of the present application includes a first occluder disc 91, a second occluder disc 92, and a waist portion 93 connecting the first occluder disc 91 with the second occluder disc 92. When the waist portion 93 is maximally pulled, its long axis is longer than or equal to 1 mm but shorter than 2 mm. The first occluder disc 91 of the first occluder in this embodiment may be any first occluder disc structure from embodiment one through embodiment six, the second occluder disc 92 in this embodiment may be any second occluder disc structure from embodiment one through embodiment six, and the waist portion 93 in this embodiment may be any waist portion structure from embodiment one through embodiment six. Therefore, this embodiment may partially or completely utilize the contents and descriptions in the above-mentioned embodiments from one through six, and duplicative language and details will not be repeated.

Figure 24:
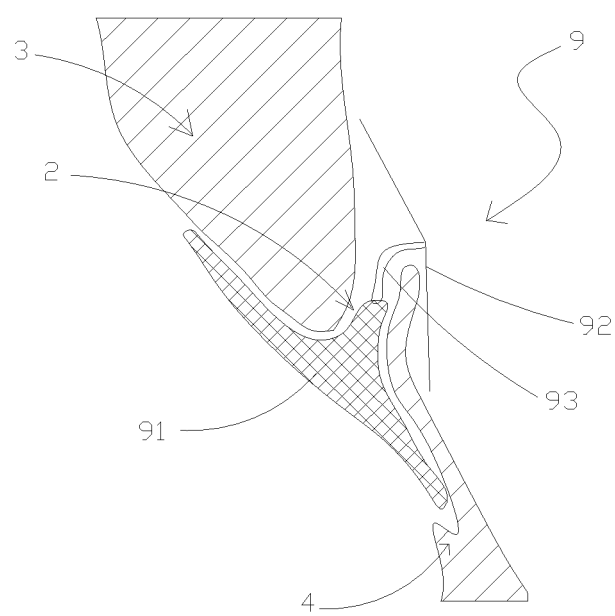
FIG. 24 is a schematic diagram of the occluder of the seventh embodiment of the present application after implantation.

With reference to FIG. 24, after the occluder 9 is implanted into a human body, the first occluder disc 91 and the second occluder disc 92 are located on two opposite sides of a PFO passageway 2 and cover an opening of the PFO passageway 2 to prevent blood from flowing into the PFO passageway; and the waist portion 93 is located in the PFO passageway 2. The length of the waist portion 93 (namely the length of the long axis of the waist portion 93 stretching maximally) is generally less than that of the PFO passageway, the waist portion 93 is in a straining state after the implantation, and starts to pull the first occluder disc 91 and the second occluder disc 92 to enable the first occluder disc 91 and the second occluder disc 92 to cling to a tissue wall at the periphery of the opening of the PFO passageway to avoid formation of a residual shunt passageway due to poor fitting between the two occluder discs and the tissue wall, thereby improving the occluding effect of the occluder. During pulling of the waist portion 93, one of the first occluder disc 91 and the second occluder disc 92, which easily deforms under the pulling action of the waist portion 93, is pulled by the waist portion 93 into the PFO passageway to compensate the deficiency of the length of the waist portion 93. The compensated waist portion 93 is as long as the PFO passageway, thereby guaranteeing the stability and the occlusion performance of the occluder.

For example, the first occluder disc 91 may include a multi-order woven structure which is the same or similar as the first occluder disc 51 in the first embodiment, it can be more desirable for the first occluder disc 91 to enter the PFO passageway 2 to compensate the waist portion under the pulling action of the waist portion 93. That is to say, the first occluder disc 91 includes a first order of woven mesh woven by multiple first order weaving filaments and a second order of woven mesh jointly woven by the multiple first order weaving filaments and multiple second order weaving filaments; and the second order of woven mesh is farther from the waist portion 93 than the first order of woven mesh. The waist portion 93 may be connected with the first order of woven mesh to realize connection between the waist portion and the first occluder disc 91. In addition, a central hole is formed in an edge, which is closely adjacent to the waist portion 93, on the first order of woven mesh, and the waist portion 93 may be further distributed around the central hole.

After the occluder 9 is implanted, under the pulling action of the waist portion 93, the first order of woven mesh, which is relatively soft and loose, deforms more easily than other portions of the first occluder disc 91 and is easily pulled by the waist portion 93 into the PFO passageway 2, thereby avoiding the phenomenon that the first occluder disc 91 is too hard to enter the PFO passageway and reducing wear of the weaving filaments on the tissue wall. In addition, the second order of woven mesh in the first occluder disc 91 deforms and enters the PFO passageway hardly under the pulling action of the waist portion 93 due to its greater hardness than the first order of woven mesh, which is formed by a relatively large number of weaving filaments and relatively dense woven grids, thereby preventing too many portions of the first occluder disc 91 from entering the PFO passageway, also preventing the first occluder disc 91 from entering the PFO passageway too easily, ensuring that the waist portion 93 may maintain the straining state after the implantation and avoiding the phenomenon that a connection wire of the waist portion 93 is in a loose state after the implantation; and therefore, the first occluder disc 91 and the second occluder disc 92 may both cling to the tissue wall to form effective occlusion.

In addition, by this arrangement, the length applicability of the waist portion of the occluder may be expanded, namely the waist portion with the same length may be applicable to PFO passageways with different lengths. During surgery, a doctor can select the occluder of a small specification for ordinary patients, so that the universality of the occluder is improved, and such operation that the doctor had to measure the length of the PFO passageway to select the specification of the occluder is avoided as far as possible; and therefore, the surgical operation difficulty is reduced, and the surgical operation time is shortened.

All technical features of the above-mentioned embodiments may be combined, as desired. In order to make the description concise, not all possible combinations of all the technical features in the above-mentioned embodiments are described, but if only the combinations of these technical features have no contradictions, they shall all be deemed to fall within the scope of the described.

The above-mentioned embodiments only express several implementation modes of the present application, and their descriptions are relatively specific and particular, but not intended to limit the scope of the invention patent. It should be noted that a person of ordinary skill in the art can further make a variety of deformations and improvements without departing from the concept of the present application, and these deformations and improvements shall all fall within the protection scope of the present application. Therefore, the protection scope of the invention patent shall be based on attached claims.

The invention claimed is:

1. An occluder, comprising a first occluder disc, a second occluder disc, and a waist portion connecting the first occluder disc with the second occluder disc, wherein the occluder further comprises a plurality of loosened lamelliform filament bundle structures distributed around the waist portion; each lamelliform filament bundle structure is wound by eight or more filaments with a diameter of 0.01 to 0.2 mm;

wherein at least one end of the each lamelliform filament bundle structure is impending freely; wherein the each lamelliform filament bundle structure is disposed on at least one of two opposite disc surfaces of the first occluder disc and the second occluder disc, and is proximate to the waist portion.

2. The occluder according to claim 1, wherein a middle portion of the each lamelliform filament bundle structure is connected with one of the two opposite disc surfaces, and two ends of the each lamelliform filament bundle structure are impending freely.

3. The occluder according to claim 1, wherein the lamelliform filament bundle structures are spaced from one another, or at least part of the lamelliform filament bundle structures are gathered and connected together on one of the two opposite disc surfaces.

4. The occluder according to claim 3, wherein one end of at least one lamelliform filament bundle structure is connected with one of the two opposite disc surfaces the, and the other end of the at least one lamelliform filament bundle structure is impending freely; and/or a middle portion of the at least one lamelliform filament bundle structure is connected with one of the two opposite disc surfaces, and two ends of the at least one lamelliform filament bundle structure are impending freely.

5. The occluder according to claim 1, wherein the filament bundle structures are loosely intertwined on one of the two opposite disc surfaces.

6. The occluder according to claim 5, wherein the one of the two opposite disc surfaces comprises a filament woven structure; and the filament bundle structures are intertwined on at least one part of weaving filaments of the one of the two opposite disc surfaces and/or the filament bundle structures pass through multiple woven grids of the one of the two opposite disc surfaces in an interpenetrating manner.

7. The occluder according to claim 1, wherein the waist portion comprises at least one connection wire which connects the two opposite disc surfaces of the first occluder disc and the second occluder disc; or the waist portion comprises a plurality of closed rings, and each closed ring is connected with the two opposite disc surfaces of the first occluder disc and the second occluder disc through one independent connection wire; or the waist portion is a multi-turn closed coil formed by penetrating one connection wire through the two opposite disc surfaces of the first occluder disc and the second occluder disc in a reciprocating manner.

8. The occluder according to claim 1, wherein the filament bundle structures are at least disposed on a disc surface of the first occluder disc which faces to the second occluder disc; the disc surface of the first occluder disc is woven by elastic weaving filaments, and comprises a central region and an edge region surrounding the central region; when the central region and the edge region are respectively compressed to a minimum in a radial direction, the maximum cross-sectional area of the central region subjected to the radial compression is smaller than the minimum cross-sectional area of the edge region subjected to the radial compression; and the waist portion is connected with the central region.

9. The occluder according to claim 8, wherein the disc surface of the first occluder disc, which faces to the second occluder disc, comprises a central hole; the first occluder disc comprises a multi-order woven mesh; the central region comprises a first order of woven mesh which is closest to the central hole and is woven by multiple first order weaving filaments; the edge region comprises a second order of woven mesh which is jointly woven by a plurality of first order weaving filaments and a plurality of second order weaving filaments and is farther from the waist portion than the first order of woven mesh; and the waist portion is connected with the first order of woven mesh.

10. The occluder according to claim 9, wherein the filament bundle structures are disposed on the first order of woven mesh.

11. The occluder according to claim 10, wherein there are not more than 72 first order weaving filaments with a diameter ranging from 0.08 mm to 0.15 mm.

12. The occluder according to claim 1, wherein the filament bundle structures are at least disposed on a disc surface of the first occluder disc, which faces to the second occluder disc; in a naturally unfolded state, an edge of the first occluder disc is bent towards the second occluder disc, thus forming a flange; at least one portion of the second occluder disc is sunken into a region formed by the flange in an encircling manner; or the second occluder disc is located outside the region formed by the flange in the encircling manner.

13. The occluder according to claim 1, wherein the second occluder disc is a single-layer disc woven by elastic weaving filaments and comprises an interlocking structure and multiple supporting rods radiating from the center; the multiple supporting rods are connected into a whole through the interlocking structure; and the whole second occluder disc is a flat structure, and all portions of the second occluder disc are uniform in thickness.

14. The occluder according to claim 13, wherein, in a region near the center of the second occluder disc, each weaving filament of one of the multiple supporting rods is overlapped with the multiple weaving filaments of other multiple supporting rods in sequence, thus forming the interlocking structure.

15. The occluder according to claim 14, wherein the multiple supporting rods are disposed in pairs; and each pair of supporting rods is located on the same diameter of the second occluder disc.

16. The occluder according to claim 15, wherein each pair of supporting rods is woven by the same group of elastic weaving filaments; the group of elastic weaving filaments of each pair of supporting rods is divided into two subgroups; and the two subgroups of elastic weaving filaments respectively bypass a central point of the interlocking structure from two sides of the central point.

17. The occluder according to claim 13, wherein one section of each supporting rod proximate a tail end has a spring shape.

* * * * *